United States Patent [19]

Inaba et al.

[11] Patent Number: 5,245,029

[45] Date of Patent: Sep. 14, 1993

[54] ION EXCHANGE PURIFICATION METHOD OF AQUEOUS CAPROLACTAM SOLUTION

[75] Inventors: Yukio Inaba; Yasuhiro Kurokawa; Takafumi Hirakawa; Kanji Oyama, all of Ube, Japan

[73] Assignee: UBE Industries, Ltd., Yamaguchi, Japan

[21] Appl. No.: 792,413

[22] Filed: Nov. 15, 1991

[30] Foreign Application Priority Data

Nov. 21, 1990 [JP] Japan .................... 2-314204

[51] Int. Cl.$^5$ .................................. C07D 201/16
[52] U.S. Cl. .................... 540/540; 540/456
[58] Field of Search .................... 540/540, 456

[56] References Cited

U.S. PATENT DOCUMENTS

| | | | |
|---|---|---|---|
| 2,692,878 | 10/1954 | Kahr | 540/540 |
| 2,758,991 | 8/1956 | Kretzers et al. | 540/540 |
| 2,828,307 | 3/1958 | Soeterbroek | 540/540 |
| 3,145,198 | 8/1964 | Mordidelli et al. | 540/540 |
| 3,470,153 | 9/1969 | Shultze et al. | 540/464 |
| 3,544,562 | 12/1970 | Schuttze et al. | 540/464 |

*Primary Examiner*—Robert T. Bond
*Attorney, Agent, or Firm*—Finnegan, Henderson, Farabow, Garrett & Dunner

[57] ABSTRACT

Disclosed is an ion exchange purification method of an aqueous caprolactam solution in a process for producing caprolactam and laurolactam by subjecting a mixture of cyclohexanone oxime and cyclododecanone oxime to Beckmann rearrangement in the presence of sulfuric acid and fuming sulfuric acid, which comprises, after neutralization of the rearrangement reaction products, and first extraction thereof with an organic solvent and second extraction of the first extract with water to obtain a second extract of an aqueous caprolactam solution, treating the aqueous caprolactam solution obtained by extraction with an organic solvent immiscible with water with a strongly acidic cation exchange resin, and subsequently with a weakly basic anion exchange resin or further with a strongly basic anion exchange resin.

11 Claims, No Drawings

ION EXCHANGE PURIFICATION METHOD OF AQUEOUS CAPROLACTAM SOLUTION

BACKGROUND OF THE INVENTION

This invention relates to an ion exchange purification method of an aqueous caprolactam solution. Particularly, the present invention relates to an ion exchange purification method of an aqueous caprolactam solution, which comprises purifying a crude aqueous caprolactam solution obtained in the intermediate stage in a process for producing caprolactam and laurolactam, by subjecting a mixture of cyclohexanone oxime and cyclododecanone oxime to Beckmann rearrangement in the presence of sulfuric acid and fuming sulfuric acid, by use of a suitable combination of ion exchange resins.

As the process for producing caprolactam and laurolactam, a process which comprises oximizing a mixture of cyclohexanone and cyclododecanone, subjecting a mixture of the cyclohexanone oxime or a salt thereof and the cyclododecanone oxime or a salt thereof produced to Beckmann rearrangement in the presence of sulfuric acid or fuming sulfuric acid, subsequently neutralizing the product with ammonia gas or ammonia water to obtain a lactam mixture, extracting the lactam mixture with an organic solvent immiscible with water or extracting the lactam oil layer separated from the aqueous ammonium sulfate by layer separation of the lactam mixture (hereinafter called lactam oil) with an organic solvent immiscible with water to obtain a first extract containing the lactam component, further reverse extracting the organic solvent extract (first extract) with water to transfer caprolactam to the aqueous layer (second extract), while having laurolactam remain in the organic solvent layer (hereinafter called the co-lactamization method) has been known in the art (for example, Japanese Patent Publication No. 7254/1971).

On the other hand, it has been well known in the art that some of the caprolactams to be used as the starting material for polyamides are required to be of extremely high purity, and various purification methods such as recrystallization, treatment with ion exchange resins, oxidation purification, etc. have been proposed. Among them, treatment with ion exchange resins has been known to be an effective method (for example, Japanese Patent Publication No. 6217/1968).

However, in the simultaneous production process of caprolactam and laurolactam by the co-lactamization method, in the aqueous caprolactam solution obtained by water extraction (second extract) of the organic solvent extract (first extract) containing the above lactam components, there exist anionic surface active substances specific in the co-lactamization such as alkyl sulfates due to higher alkyl alcohols such as linear or branched dodecyl alcohol, etc. contained in cyclododecanone which is the starting material. Also, the impurities which are water-soluble colored impurities formed in the Beckmann rearrangement and migrated into the organic solvent layer by droplet accompaniment, etc. in the organic solvent extraction (first extraction) of the lactam oil will be migrated into the aqueous layer in water extraction (second extraction). Accordingly, the present inventors have previously proposed to remove the impurities by treating an aqueous caprolactam solution (said second extract) containing these impurities with an ion exchange resin (for example, Japanese Patent Application No. 151572/1990), but alkyl sulfates such as dodecyl sulfate, etc. are strongly adsorbed on strongly basic anion exchange resins to such extent as almost impossible of desorption in ion exchange resin purification, whereby there is involved the problem that regeneration use of ion exchange resins can be done with difficulty.

SUMMARY OF THE INVENTION

An object of the present invention is to solve the problems as described above and provide an ion exchange purification method of an aqueous caprolactam solution which removes surface active substances which are impurities in aqueous caprolactam solutions economically efficiently.

The present inventors have therefore studied intensively, and consequently found that surface active substances such as alkyl sulfates, etc. can be removed by a specific combination of ion exchange resins, and also ion exchange resins can be regenerated and used, to accomplish the present invention.

More specifically, the present invention is an ion exchange purification method of an aqueous caprolactam solution in a process for producing caprolactam and laurolactam by subjecting a mixture of cyclohexanone oxime and cyclododecanone oxime to Beckmann rearrangement in the presence of sulfuric acid and fuming sulfuric acid, which comprises, after neutralization of the rearrangement reaction products, and first extraction thereof with an organic solvent immiscible with water to obtain a first extract of an organic solvent extract and second extraction of the first extract with water to obtain a second extract of an aqueous caprolactam solution treating the aqueous caprolactam solution with a strongly acidic cation exchange resin, and subsequently with a weakly basic anion exchange resin or further with a strongly basic anion exchange resin.

DETAILED DESCRIPTION OF THE INVENTION

As the strongly acidic cation exchange resin to be used in the present invention, styrene-divinylbenzene copolymers having sulfonic groups, etc. may be exemplified. As the example of the styrene-divinylbenzene copolymer having sulfonic group, there may be included Amberlite 252 (trade name, MR type, manufactured by Rohm and Haas company), Amberlite 200C (trade name, MR type, manufactured by Rohm and Haas Company), Amberlite 200CT (trade name, MR type, manufactured by Rohm and Haas Company), Amberlite 200CP (trade name, MR type, manufactured by Rohm and Haas Company), Amberlite IR-120B (trade name, Gel type, manufactured by Rohm and Haas Company), Amberlite IR-122 (trade name, Gel type, manufactured by Rohm and Haas Company), Diaion P.K-220 (trade name, manufactured by Mitsubishi Kasei Kogyo K.K.).

As the weakly basic anion exchange resin, anion exchange resins having secondary or tertiary amino groups may be exemplified, but preferably those having tertiary amino groups. As the typical example of the weakly basic anion exchange resin, there may be included Amberlite IRA-35 (trade name, MR type, manufactured by Rohm and Haas Company), Amberlite IRA-68 (trade name, Gel type, manufactured by Rohm and Haas Company), Diaion WA20 (trade name, manufactured by Mitsubishi Kasei Kogyo K.K.),.etc.

As the strongly basic anion exchange resins, anion exchange resins having quaternary ammonium groups may be exemplified. As the strongly basic anion exchange resins, there may be included Amberlite IRA-900 (trade name, MR type, manufactured by Rohm and Haas Company), Amberlite IRA-420 (trade name, Gel type, manufactured by Rohm and Haas Company), etc. Also, use of an ion exchange resin having macroporosity is preferable.

As the three type ion exchange resins, it is preferable to use MR type ion exchange resin than Gel type ion exchange resin, since the molecular weight of the impurity is relatively large. Because even in the case of adsorption and desorption (reproduction), the impurity is easily moved in the MR (macro-reticular) type ion exchange resin having a macro pore structure than in the Gel type ion exchange resin having a small core diameter.

For performing efficiently adsorption-separation of the impurities at cation exchange resin and anion exchange resin, the concentration of the aqueous caprolactam solution (second extraction) to be treated may be preferably 5 to 90%, more preferably 5 to 70%.

The treatment rate of the aqueous caprolactam solution may be 20 m$^3$/hr·m$^3$ resin or lower, preferably 6 m$^3$/hr·m$^3$ resin or lower, as represented by loaded flow rate relative to the ion exchange resin.

The treatment temperature of the aqueous caprolactam solution may be preferably 20° to 100° C., more preferably 40° to 70° C.

For the regeneration method of ion exchange resins, those generally known can be utilized. More specifically, for the regeneration method of the cation exchange resin, there are (a) the method in which regeneration is effected with an aqueous sulfuric acid solution after passage of an aqueous caustic soda solution, (b) the method in which regeneration is effected only with an aqueous sulfuric acid solution, but the method (b) is preferable. For the regeneration method of the anion exchange resin, there are (a) the method in which regeneration is effected with an aqueous caustic soda solution after passage of an aqueous sulfuric acid solution, (b) the method in which regeneration is effected with an aqueous sodium chloride solution, (c) the method in which regeneration is effected only with an aqueous caustic soda solution, and (d) the method in which regeneration is effected with an aqueous sodium chloride solution and an aqueous caustic soda solution, but the method (c) is preferable among these methods. In the method wherein regeneration is effected with the use of an aqueous sodium chloride solution, unless washing is sufficient, the sodium chloride remaining on the resin will be mixed into the aqueous caprolactam solution, whereby there is an anxiety that device corrosion may occur in concentration and distillation steps of the aqueous caprolactam solution, and therefore there is the problem that the amount of water discharged is increased by washing of the resin. When regeneration is effected only with an aqueous caustic soda solution, conventional austenite type stainless steel can be used.

The concentration of the regeneration liquid may be preferably 1 to 10% by weight in either case.

The present invention is described in more detail below by referring to Examples, but its scope will not be limited by these.

Preparation example of aqueous caprolactam solution:

An amount 5.2 Kg of an organic material (hereinafter called lactam oil) containing primarily 40% by weight of caprolactam, 44% by weight of laurolactam and 12% by weight of water obtained by subjecting the product obtained by oximizing a mixture of cyclohexanone and cyclododecanone to Beckmann rearrangement in the presence of sulfuric acid, then neutralizing the product with ammonia, followed by separation of the aqueous ammonium sulfate layer phase separated was charged into a reaction vessel made of a glass (volume 50 liter) equipped with a stirrer, and then 19 kg of toluene was added, the mixture mixed under stirring at a temperature of 70° C. and then left to stand,, followed by withdrawal of the aqueous layer separated as the heavy liquid. Subsequently, the toluene extract (first extract) separated from the heavy liquid was cooled to 50° C., and the heavy liquid further separated was withdrawn.

To the toluene extract obtained was added 22 kg of water, the mixture stirred and mixed at 58° to 63° C., and the caprolactam was reverse extracted to the aqueous layer side (second extract), whereby 20 kg of an organic phase (toluene layer) containing 10.7% by weight of laurolactam and 21 kg of an aqueous phase containing 6.4% by weight of caprolactam were obtained.

The operations as described above were repeated three times, and the second extract of the aqueous caprolactam solution obtained was concentrated under a vacuum of 50 mmHg to give 13.5 Kg of an aqueous solution controlled to the concentration of caprolactam to 30% (hereinafter called lactam water).

EXAMPLE 1

The lactam water (the aqueous coprolactam solution; second extract) obtained in Preparation example was fed through a first tower glass column filled with 60 ml of a strongly acidic cation exchange resin (trade name: Amberlite IR200C, manufactured by Rohm and Haas Company) and a second tower glass column filled with 20 ml of a weakly basic anion exchange resin (trade name: Amberlite IRA-35, manufactured by Rohm and Haas Company) at a temperature of 45° C. and a feeding rate of 100 ml/hr for 30 hours.

And, the aqueous lactam solution obtained by carrying out the ion exchange treatment was concentrated to a concentration of 90% under a pressure of 50 mm Hg, and 0.16% of caustic soda based on the pure lactam component in the concentrate obtained was added to carry out vacuum distillation, thereby distillig out first most of the water, to obtain 46 g of the hydrous lactam initial distillate, 795 g of the main fraction and 51 g of the distillate residue.

The main fraction obtained had the quality as described below.

0.1N potassium permanganate consumption amount: 2.0 cc/kg

UV-ray transmittance (290 nm, 50% solution): 95.8%

The weakly basic anion exchange resin employed was generated with 4% aqueous caustic soda solution, and the total exchange capacity was measured to be 1.1 mg equivalents/ml resin, which was not changed from the total exchange capacity before use.

The 0.1N potassium permanganate consumption amount was determined by dissolving 100 g of caprolactam in 250 ml of sulfuric acid of 8 mol/liter concentration, titrating it with N/10 potassium permanganate solution, followed by calculation.

The UV-ray transmittance is the transmittance of UV-ray with a wavelength of 290 nm in 50% aqueous caprolactam solution, which is lowered in the presence of an impurity such as aromatic amine or azo compound.

EXAMPLE 2

The lactam water (the aqueous caprolactam solution; second extract) obtained in Preparation example was fed through a first tower glass column filled with 60 ml of a strongly acidic cation exchange resin (trade name: Amberlite IR200C, manufactured by Rohm and Haas Company), a second tower glass column filled with 20 ml of a weakly basic anion exchange resin (trade name: Ambelite IRAA-35, manufactured by Rohm and Haas Company) and a third tower glass column filled with 20 ml of a strongly basic anion exchange resin (trade name: Amberlite IRA-900, manufacutred by Rohm and Haas Company) at a temperature of 45° C. and at a feed rate of 100 ml/hr for 30 hours.

And, the aqueous lactam solution obtained by carrying out the ion exchange treatment was distilled similarly as in Example 1.

The main fraction had the quality as described below.

0.1N potassium permanganate consumption amount: 1.3 cc/kg

UV-ray transmittance (290 nm, 50% aqueous solution): 96.5%

The weakly basic ion exchange anion resin employed was regenerated with 4% aqueous caustic soda solution, and the total exchange capacity was measured to be 1.1 mg equivalent/ml resin, which was not changed from the total exchange capacity before use. Also, the strongly basic anion exchange resin was regenerated with 4% aqueous caustic soda solution, and the total exchange capacity was measured to be 0.9 mg equivalent/ml resin, which was not changed from the total exchange capacity before used.

COMPARATIVE EXAMPLE 1

The lactam water (the aqueous caprolactam solution; second extract) obtained in Preparation example was fed through a first tower glass column filled with 60 ml of a strongly acidic cation exchange resin (trade name: Amberlite IR-200C, manufactured by Rohm and Haas Company) and a seoncd tower glass column filled with 20 ml of a strongly basic anion exchange resin (trade name: Amberlite IRA-900, manufactured by Rohm and Haas Company) at a temperature of 45° C. and at a feed rate of 100 ml/hr for 30 hours.

And, the aqueous lactam solution obtained by carrying out the ion exchange treatment was distilled similarly as in Example 1.

The main fraction obtained had the quality as described below.

0.1N potassium permanganate consumption amount: 1.8 cc/kg

Uv-ray transmittance (290 nm, 50% solution): 95.2%

The strongly basic anion exchange resin employed was regenerated with 4% aqueous caustic soda solution, and the total exchange capacity was measured to be 0.1 mg equivalent/ml resin, which was found to be unregenerable as compared with the total exchange capacity of 0.9 mg equivalent/ml resin before use.

As described above, when ion exchange purification is carried out according to the method of the present invention, regeneration was found to be possible without substantially lowering the exchange capacity, but regeneration was impossible in the case of Comparative example.

We claim:

1. An ion exchange purification method of an aqueous caprolactam solution in a process for producing caprolactam and laurolactam by subjecting a mixture of cyclohexanone oxime and cyclododecanone oxime to Beckmann rearrangement in the presence of sulfuric acid and fuming sulfuric acid, which comprises, after neutralization of the rearrangement reaction products with ammonia gas or ammonia water, and first extraction thereof with an organic solvent immiscible with water to obtain a first extract of the organic solvent extract and second extraction of the first extract with water to obtain a second extract of an aqueous caprolactam solution, treating the aqueous caprolactam solution with a strongly acidic cation exchange resin, and subsequently with a weakly basic anion exchange resin, and optionally further with a strongly basic anion exchange resin.

2. The purification method of claim 1 wherein the strongly acidic cation exchange resin is a styrene-divinylbenzene copolymer having sulfonic groups.

3. The purification method of claim 1 wherein the weakly basic anion exchange resin is an anion exchange resin having secondary amino groups.

4. The purification method of claim 1 wherein the weakly basic anion exchange resin is an anion exchange resin having tertiary amino groups.

5. The purification method of claim 1 wherein the strongly basic anion exchange resin is present and is an anion exchange resins having quaternary ammonium groups.

6. The purification method of claim 1 wherein the concentration of the aqueous caprolactam solution to be treated is 5 to 90%.

7. The purification method of claim 6 wherein the concentration of the aqueous caprolactam solution to be treated is 5 to 70%.

8. The purification method of claim 1 wherein the treatment rate of the aqueous caprolactam solution is 20 $m^3/hr \cdot m^3$ resin or lower.

9. The purification method of claim 8 wherein the treatment rate of the aqueous caprolactam solution is 6 $m^3/hr \cdot m^3$ resin or lower.

10. The purification method of claim 1 wherein the treatment temperature of the aqueous caprolactam solution is 20° to 100° C.

11. The purification method of claim 10 wherein the treatment temperature of the aqueous caprolactam solution is 40° to 70° C.

* * * * *

UNITED STATES PATENT AND TRADEMARK OFFICE
CERTIFICATE OF CORRECTION

PATENT NO. : 5,245,029
DATED : September 14, 1993
INVENTOR(S) : Yukio INABA et al.

It is certified that error appears in the above-indentified patent and that said Letters Patent is hereby corrected as shown below:

Claim 5, column 6, line 39, change "resins" to --resin--.

Signed and Sealed this

Twentieth Day of September, 1994

Attest:

BRUCE LEHMAN

*Attesting Officer*  *Commissioner of Patents and Trademarks*